United States Patent [19]
Steinhaus et al.

[11] Patent Number: 5,201,808
[45] Date of Patent: Apr. 13, 1993

[54] MINUTE VOLUME RATE-RESPONSIVE PACEMAKER EMPLOYING IMPEDANCE SENSING ON A UNIPOLAR LEAD

[75] Inventors: Bruce M. Steinhaus, Parker; Tibor A. Nappholz, Englewood; James A. Nolan, Conifer; Robert A. Morris, Palmer Lake, all of Colo.

[73] Assignee: Telectronics Pacing Systems, Inc., Englewood, Colo.

[21] Appl. No.: 833,435

[22] Filed: Feb. 10, 1992

[51] Int. Cl.$^5$ ............................................. A61N 1/365
[52] U.S. Cl. ............................................. 128/419 PG
[58] Field of Search ................................. 128/419 PG

[56] References Cited

U.S. PATENT DOCUMENTS

| | | | |
|---|---|---|---|
| 4,567,892 | 2/1986 | Plicchi et al. | 128/419 PG |
| 4,596,251 | 6/1986 | Plicchi et al. | 128/419 PG |
| 4,692,719 | 9/1987 | Whigham | 332/11 D |
| 4,702,253 | 10/1987 | Nappholz et al. | 128/419 PG |
| 4,730,618 | 3/1988 | Lekholm | 128/419 PG |
| 4,901,725 | 2/1990 | Nappholz et al. | 128/419 PG |
| 4,961,423 | 10/1990 | Canducci | 128/419 PG |
| 4,976,183 | 3/1986 | Plicchi et al. | 128/419 PG |
| 5,003,976 | 4/1991 | Alt | 128/419 PG |
| 5,044,365 | 9/1991 | Webb et al. | 128/419 PG |

Primary Examiner—William E. Kamm
Attorney, Agent, or Firm—Gottlieb, Rackman & Reisman

[57] ABSTRACT

A rate-responsive pacemaker employing a rate control parameter of respiratory minute volume, derived over a unipolar lead. The pacemaker performs the minute volume measurement by periodically applying a measuring current between the lead and a reference point on the pacemaker case. This measuring current has frequency components in a range from approximately 10 kilohertz to 1000 megahertz. Application of this measuring current allows the pacemaker to detect the voltage which arises from the applied current and, from the detected voltage, to measure the patient's spatial impedance. Spatial impedance and minute volume vary as a function of the patient's pleural pressure. The pacemaker derives minute volume and rate-responsive pacing rate from the spatial impedance measurement.

44 Claims, 5 Drawing Sheets

MINUTE VOLUME RATE-RESPONSIVE PACEMAKER EMPLOYING IMPEDANCE SENSING ON A UNIPOLAR LEAD

TECHNICAL FIELD

This invention relates to rate-responsive pacemakers, and more particularly to such pacemakers in which the rate control parameter is minute volume.

DESCRIPTION OF THE PRIOR ART

U.S. Pat. No. 4,702,253, entitled "Metabolic-Demand Pacemaker and Method of Using the Same to Determine Minute Volume", which issued Oct. 27, 1987, in the names of Nappholz et al., discloses a rate-responsive pacemaker which employs minute volume as a rate control parameter. Minute volume is a measure of the amount of air inspired by a person as a function of time. The greater the amount of air inspired, the greater the need for a higher heart pacing rate. The pacemaker of the aforesaid patent (hereinafter called the "'253 pacemaker") measures minute volume by providing a three-electrode lead which employs one electrode to sense heart signals and pace the patient's heart in the conventional manner and which employs the remaining two electrodes to perform the minute volume measurement.

A three-electrode lead is not a standard lead as is known in the art of cardiac pacing. The two electrodes for measuring minute volume are located in a blood vessel in the vicinity of the patient's pleural cavity. The '253 pacemaker periodically applies current pulses between one of the electrodes and the pacemaker case, and measures the voltage which results from the applied current between the other electrode and the pacemaker case. The measured voltage is a function of the blood impedance in the vessel which, in turn, is dependent upon the pleural pressure. The '253 pacemaker determines the minute volume by monitoring the modulation in the impedance measurement.

One problem with the '253 pacemaker is that it requires a nonstandard lead, a lead having at least three electrodes. Unipolar (single electrode) and bipolar (dual electrode) leads are standard in the art of cardiac pacing. There are many patients with implanted unipolar and bipolar leads, and if a three-electrode lead is required for a new pacemaker, then a prior art non-rate-responsive pacemaker cannot be replaced by a rate-responsive pacemaker simply by exchanging pacemakers and using the same lead. Furthermore, there are physicians who like the feel of the leads they have been using in the past, and one factor which weighs against implanting a rate-responsive pacemaker might be that it requires a lead with a new feel.

U.S. Pat. No. 4,901,725, entitled "Minute Volume Rate-Responsive Pacemaker, which issued Feb. 20, 1990, in the names of Nappholz et al., discloses an improved minute volume-controlled rate-responsive pacemaker (hereinafter called the "'725 pacemaker") which can be used with a conventional bipolar lead. Such a bipolar lead has two electrodes for sensing and pacing the heart. In the '725 pacemaker a ring electrode is used additionally to apply a current which flows to the pacemaker case. A tip electrode is used to measure the blood impedance between the tip and the case in response to the current pulse applied through the ring electrode. The '725 pacemaker utilizes the measured blood impedance to derive an appropriate pacing rate.

Although the '725 pacemaker uses bipolar leads which are standard in cardiac pacing, it has a limitation in that this pacemaker cannot be used in the many patients who have had previously implanted unipolar leads. Unipolar leads, which have a single tip electrode, are also standard in the art of cardiac pacing. If a bipolar lead is required when a patient has a new pacemaker implanted, then a non-rate-responsive pacemaker that is connected to a unipolar lead cannot be replaced by a '725 rate-responsive pacemaker simply by exchanging pacemakers and using the same lead.

Previous attempts have been made to perform minute volume rate-responsive pacing in a pacemaker using unipolar leads. These attempts failed, primarily because the blood impedance signal measured from unipolar leads was too weak in comparison to system noise and other unwanted signals present. A primary source of noise, which obscures impedance signals from a unipolar lead, is the electrolytic effect at the interface between the metal electrode and body fluid electrolytes. The pacemaker generates a net charge at the electrode for pacing the heart and, in the rate-responsive pacemaker of the '253 and '725 pacemakers as well as in the pacemaker of the present invention, for measuring blood impedance. This net charge within the metal is positive at the anode and negative at the cathode of the tip and ring electrodes. An opposing charge distribution develops in the electrolyte due to the charge distribution within the electrodes. This opposing charge is held from the metal surface by the forces of reduction and oxidation chemical reactions, which occur whenever a metal is placed in an electrolytic solution. The charge separation distance is approximately the thickness of a molecular layer of water.

The charged layers at the electrode-electrolyte interface constitute a charged capacitance in which the charges are held together by electrostatic forces. The magnitude of the capacitance depends inversely on the separation of the charged surfaces. This separation is very small, on the order of the dimension of molecular water. Therefore, the capacitance is remarkably large, in the range of 1 to 20 $\mu F/cm^2$. The presence of a large capacitance at the tip electrode causes a large DC impedance. This electrolytic phenomenon creates a large, slowly decaying polarization potential at the tip electrode. When a pacemaker generates a conductive current through the tip, either for pacing the heart or measuring blood impedance, most of the sensed impedance changes are local effects of the electrode-electrolyte interface. This electrolytic phenomenon occurs in all types of leads, bipolar as well as unipolar.

It will be recalled that the '725 pacemaker generates a measuring current between the ring electrode and the case but measures the blood impedance from a separate electrode, the tip electrode, which is located generally outside the vicinity of electrolyte polarization. In the case of a pacemaker which uses a unipolar electrode, on the other hand, the measuring electrode and the current generating electrode are one and the same, and the measuring electrode is located precisely at the point of electrolyte polarization. Furthermore, the electrode tip has a very small surface area, over which the current is concentrated, leading to very large impedance changes where the electrode meets the electrolytes. Therefore, instead of measuring blood impedance as intended, a unipolar electrode constrains the pacemaker to predominantly detect the electrode-electrolyte polarization effects.

Three discoveries have led to improvements in an impedance-measuring pacemaker, providing a solution to the problem of the electrode-electrolyte polarization effect which hindered the measurement of blood impedance in prior art pacemakers. By solving this problem, the pacemaker of the present invention performs rate-responsive cardiac pacing based on the measurement of minute ventilation in a system which employs a unipolar lead.

A first discovery employed by the pacemaker of the present invention is that, by elevating the frequency content of the measuring electrical current much higher than the frequency employed in prior art impedance measuring devices, the nature of the measuring current changes from a conduction current to predominantly a displacement current. At high frequencies a pacemaker lead can be viewed as a leaky conductor, or signal radiator. At higher measuring frequencies, more of the signal leaks from the lead throughout its length. The lead will measure the spatial impedance of the medium surrounding the lead. This is different from the measurement of "blood impedance", by means of interrogation using conduction current, as was performed in the '253 and '725 pacemakers. The pacemaker of the present invention performs the measurement through the length of the lead, not at the tip electrode. The tip electrode is separated from the input to the lead by the resistance, inductance and distributed capacitance of the lead. At higher measuring frequencies, these components of the lead impedance cause the flow of current along the lead to induce displacement currents in the tissue. Once the signal leaves the electrode tip, the current becomes a conduction current, creating the ionic conditions which make up the electrode-electrolyte polarization effect. The higher measuring current frequencies of the present invention greatly reduce the electrode-electrolyte polarization effect.

The aforementioned characteristics of the electrolytic phenomenon, in which a large capacitance at the tip electrode causes a large DC impedance, will be recalled. For higher frequency currents, such as alternating currents or current pulses, this capacitive impedance becomes much less than the resistance of the electrodes and electrolytic solutions within the blood and body fluids, reducing unwanted effects from the electrode-electrolyte interface. The applied measuring current may be in the form of high frequency continuous wave current, short duration current pulses, or timed pulses of continuous wave current. The effect of the higher frequency measuring current is to change the character of the applied measuring current from a conductive current to a displacement current. Pacemakers of the prior art measured impedance by detecting changes in voltage in response to a current of a lower frequency or a longer pulse width than the pacemaker of the present invention, in which case the current flowed in a conductive manner through the blood and the electrode and polarization noise problems arose.

The pacemaker of the present invention employs high frequency measuring current which creates a displacement current within the body, with little net current injected into the body. The pacemaker creates this displacement current by generating an electrical current which flows within the conductor of the lead. This conductor is separated from the patient's body and its electrolytes by a layer of electrical insulation at the outside surface of the lead. The current within the lead generates an electrical field which creates the displacement current in the body.

Upon the generation of this coupled ionic field, a displacement current arises in the body which allows the pacemaker to detect impedance changes in the body remote from the location in which electrode-electrolyte artifacts arise. In this manner the pacemaker of the present invention reduces the impedance effects of the tip electrode. The high frequency measuring current radiates more energy into the body along the lead and less to the tip, to reduce local artifact effects and inject less current into the heart. The reduction of local artifact effects greatly improves the signal quality of the measurement. This improvement in signal quality provides for a more accurate and reliable impedance measurement and a more effective derivation of pacing rate in response to metabolic needs.

Although the main benefit of generating a high frequency measuring current is to allow sensing of impedance by reducing interface polarization effects, the generation of a measuring current in this manner provides for other important advantages. Because the pacemaker measures a displacement current rather than a conductive current, for the purpose of measuring impedance the pacemaker case may be completely insulated. It is desirable to insulate a pacemaker case, at least partially, to prevent the pacemaker from stimulating skeletal muscles upon pulse generation, causing "muscle tics" which are irritating to the patient. The '725 pacemaker required that a large portion of the pacemaker case remain free of insulation so that current could flow in a conductive manner between the ring electrode and the case to allow measurement of blood impedance. However, unipolar pacing pulse generation requires a tiny patch of the pacemaker case to remain without insulation. The ability to reduce the size of the conductive patch on the pacemaker case is extremely advantageous for preventing skeletal muscle stimulation, caused by the generation of either pacing pulses or measuring current.

Impedance measuring devices which are known in the prior art, including the '253 and '725 pacemakers, perform measuring interrogation using current pulses of longer duration than the pulses of the present invention. A pacemaker which generates short duration current pulses has the advantage of requiring a lower energy expenditure to perform the impedance measurement. A lower energy expenditure provides for a longer pacemaker lifetime.

Another advantage of performing impedance measurements using short duration current pulses or timed pulses of continuous wave currents is that less energy is injected into the heart. This results in a lesser danger of stimulating the heart with the measuring current. Furthermore, the longer duration current pulses of prior art impedance measuring devices often create artifacts which obscure electrocardiogram (ECG) or intracardiac electrogram (IECG) signals which are sensed either by the impedance measuring device or a separate signal monitoring device.

A second discovery leading to the implementation of the pacemaker of the present invention is the finding that, by selecting different values of measuring current frequency or pulse width, the pacemaker can "tune" the impedance sensor to measure a particular type of signal and reject unwanted signals and other noise. Rather than measuring the impedance essentially between the tip electrode and the case as was done in prior art devices, the pacemaker of the present invention measures the impedance between the input of the lead to the pacemaker and the pacemaker case. The pacemaker senses body impedance along the entire length of the lead. The impedance at the lead input is the impedance due to multiple reflections of the signal along the lead due to the properties of the lead and the medium surrounding it. At high measuring frequencies, a larger portion of the signal leaks from the lead close to the case. At lower measuring frequencies, more of the signal will leak from the lead further along the lead. Some of the sensed signals may be physiological, others may arise from intrinsic sources. For example, at a particular range of measuring current frequencies, respiration signals predominate. At another range of frequencies, cardiac stroke volume signals will dominate. At still another range of frequencies, noise caused by motion may be the primary signal. The pacemaker of the present invention employs a measuring current frequency which best selects respiration signals. The measuring current includes higher frequency components to avoid interface electrolytic phenomenon, but not so elevated in frequency that motion artifacts become large in relation to the respiratory signal.

A third discovery which may be employed in the pacemaker of the present invention is the importance of matching the source impedance of the measuring circuit to the impedance of the body. Impedance matching greatly enhances the signal to noise ratio of the measured impedance signal.

SUMMARY OF THE INVENTION

In accordance with one aspect of the present invention, there is provided a rate-responsive pacemaker comprising a means for pulsing a patient's heart at a controlled rate by generating stimulation pulses and coupling these pulses to the heart via a unipolar lead. This controlled rate is automatically derived by the pacemaker, based upon a measurement of the patient's respiratory minute volume. The pacemaker performs this minute volume measurement using a spatial impedance measuring means which periodically applies a measuring current between the pacemaker lead and a reference point on the pacemaker case. The spatial impedance measuring means generates this measuring current using a circuit which holds constant either the measuring current or the measuring voltage. The measuring current has a majority of frequency components in a range from approximately 10 kilohertz to 1000 megahertz. The spatial impedance measuring means measures the impedance between the lead and the reference point in response to the application of the measuring current. Spatial impedance varies as a function of the patient's pleural pressure which, in turn, varies as a function of minute volume. The pacemaker includes a means for deriving minute volume from the spatial impedance measurement.

In one embodiment which incorporates this aspect of the present invention, the pacemaker generates measuring current in the form of short duration pulses. Signals from different sources, both physiological and non-physiological in origin, may be mutually distinguished by interrogating the body with current pulses of various durations. Previous clinical tests provide the relationships of pulse duration to signals of particular origins. These relationships are encoded within the pacemaker. The pacemaker may select and control the width of these pulses to detect at least one particular type of physiological or non-physiological signal. Alternatively, the pacemaker may select and control the width of these pulses to remove signal components of at least one particular type of physiological or non-physiological signal.

In another embodiment which incorporates this aspect of the present invention, the pacemaker generates measuring current in the form of high frequency continuous waves. Signals from different sources, both physiological and non-physiological in origin, may be mutually distinguished by interrogating the body with current of various frequencies. Previous clinical tests provide the relationships of frequency to signals of particular origins. These relationships are encoded within the pacemaker. The pacemaker may select and control interrogation frequency to detect at least one particular type of physiological or non-physiological signal. Alternatively, the pacemaker may select and control interrogation frequency to remove signal components of at least one particular type of physiological or non-physiological signal.

In a further embodiment which incorporates this aspect of the present invention, the pacemaker generates measuring current in the form of timed pulses of high frequency continuous waves. This embodiment of a pacemaker functions in a similar manner to the continuous wave pacemaker embodiment discussed in the preceding paragraph.

In accordance with another aspect of the present invention, there is provided a rate-responsive pacemaker comprising a means for pulsing a patient's heart at a controlled rate by generating stimulation pulses and coupling these pulses to the heart via a unipolar lead. This controlled rate is automatically derived by the pacemaker, based upon a measurement of the patient's spatial impedance signal. The pacemaker performs this spatial impedance measurement using a current generating means which periodically applies a measuring current between the lead and a reference point on the pacemaker case. This measuring current has a majority of frequency components in a range from approximately 10 kilohertz to 1000 megahertz. A measuring means measures the spatial impedance between the lead, at the location of its interface with the pacemaker, and the reference point. This spatial impedance results from the application of the measuring current by the generating means. Spatial impedance varies as a function of the patient's pleural pressure which, in turn, varies as a function of minute volume.

BRIEF DESCRIPTION OF THE DRAWINGS

Further objects, features and advantages of the invention will become apparent upon consideration of the following detailed description, taken in conjunction with the accompanying drawings, in which.

DETAILED DESCRIPTION

Figure 1:
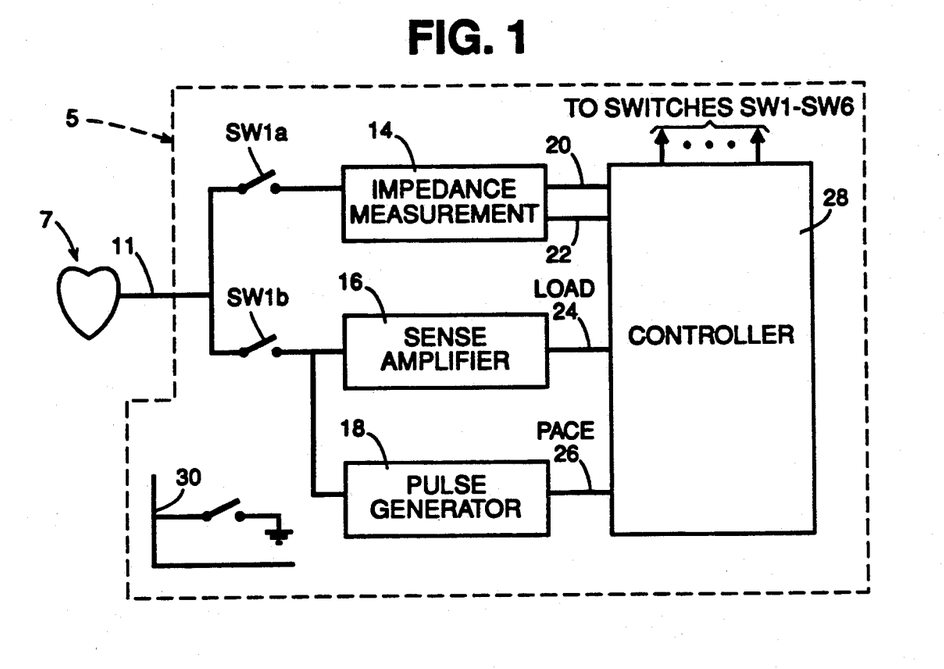
FIG. 1 is a block diagram of an illustrative embodiment of the invention.
Figure 8:
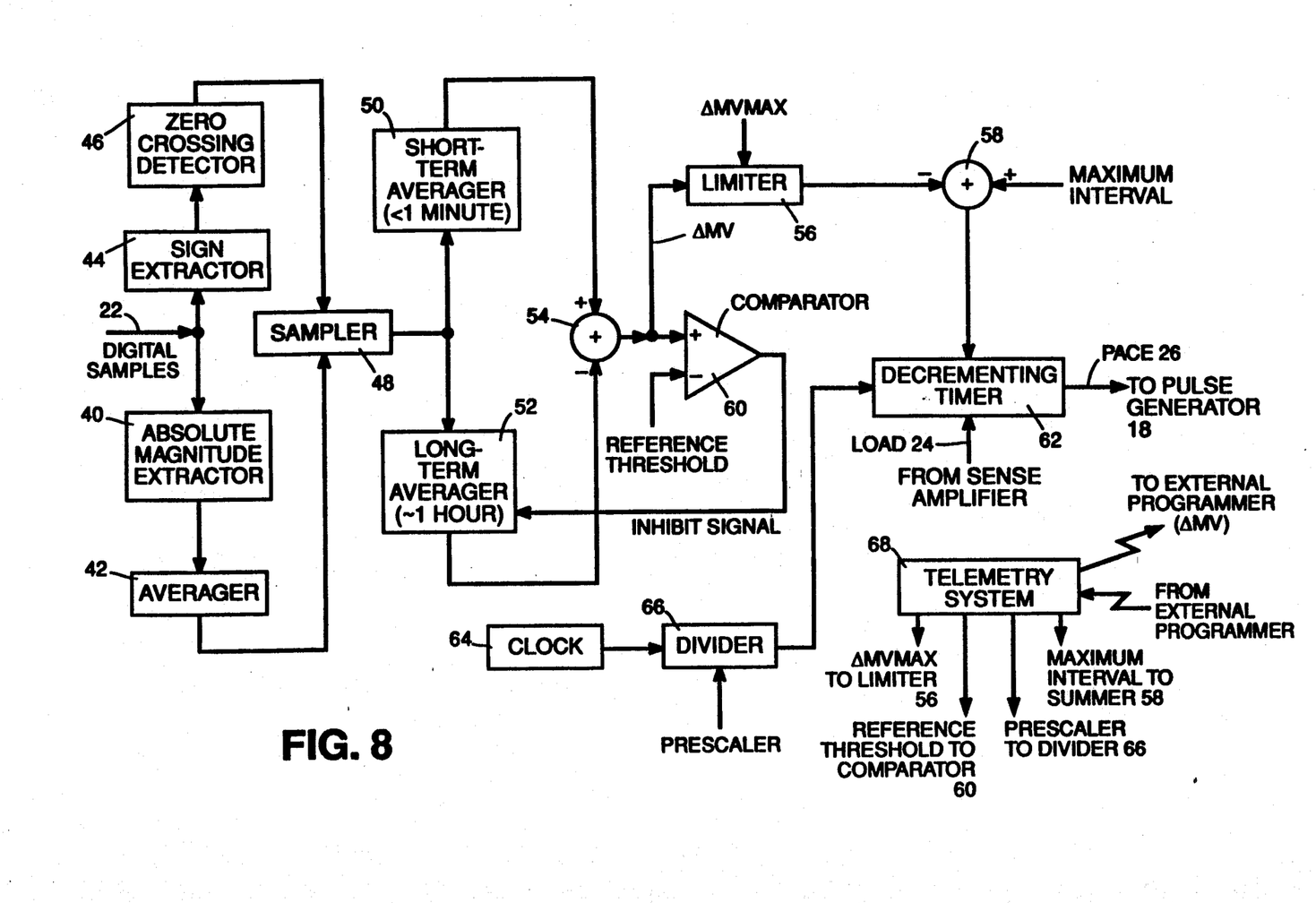

The drawing of FIG. 1 is a high-level block schematic of a pacemaker, shown generally at 5. All pacemaker logic is under the control of a controller 28 (which may include a microprocessor, although discrete blocks are shown in FIG. 8). The controller operates various switches in the pacemaker, of which only one pair SW1a, SW1b is shown. Switch SW1B is closed whenever the pacemaker is to pace or sense.

Figure 2:
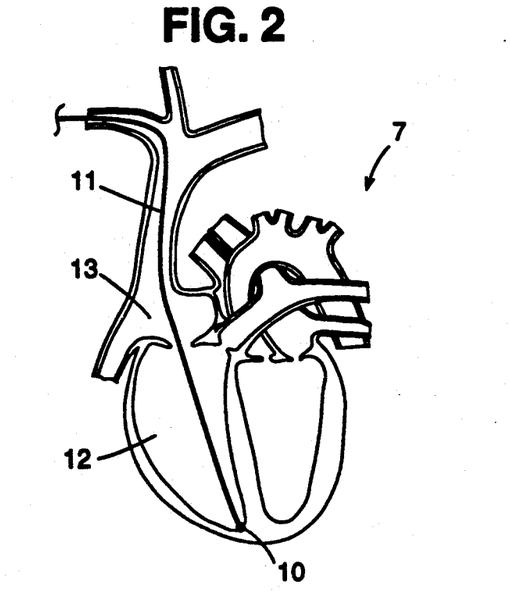
FIG. 2 depicts placement in a patient's right ventricle of a conventional unipolar lead which may be used to effect minute volume measurements, along with pacing and sensing.

Referring to FIGS. 1 and 2, together, in order to pace, the controller 28 sends a command to a pulse generator 18 by means of a signal on a PACE conductor 26. The pulse generator 18 responds to this command by applying a current pulse through the switch SW1b and a conventional unipolar lead 11 to the latter's tip electrode 10, which is shown positioned in the right ventricle 12 of a patient's heart 7 in FIG. 2. A sense amplifier 16 senses a cardiac signal on the electrode. (Various functions well known in the art, such as blanking of the sense amplifier during pacing, are not shown inasmuch as they have no bearing on the subject invention.) The sensing of a heartbeat, spontaneous or evoked, results in a pulse appearing on LOAD conductor 24 and being delivered to controller 28. (The "load" function initiates the loading of an initial value in timer 62 of FIG. 8, as will be described hereinafter.)

The pacemaker makes an impedance measurement when the controller 28 pulses the conductor 20 to activate impedance measurement block 14. Upon this event, switch SW1a closes and switch SW2a opens and impedance measurement block 14 applies a current to the lead 11, causing current to flow through the lead toward the tip electrode 10. The measuring current which is applied to the electrode has frequency characteristics in the range from about 10 kHz to about 1000 MHz. At these measuring current frequencies, the lead acts as an antenna which creates a displacement current in the body. This displacement current is fundamentally different from the conduction current which is generated by prior art impedance measuring pacemakers such as the '253 and '725 pacemakers. The impedance measuring block 14 may generate this measuring current in the form of continuous wave current, short-duration pulses of current, or timed pulses of continuous wave current. The impedance measurement block 14 measures spatial impedance by determining the potential between the pacemaker case 30 and the pacemaker input connection to the conductor (not shown) within lead 11. This conductor extends to the tip electrode 10. In this configuration, the pacemaker case 30 serves as a reference potential for the pacemaker circuitry. In the preferred embodiment of the pacemaker, the impedance measurement block 14 derives samples at a rate of about 20 per second and communicates these samples to controller 28 over conductor 22. The impedance measurement can be executed as described in the aforementioned '253 patent.

Placement of the unipolar lead is shown in FIG. 2. The tip electrode 10 makes contact with the wall of the right ventricle 12 or the right atrium 13 of the patient's heart 7. When the impedance measurement block generates measuring currents at appropriate frequencies, as will be described hereinafter, the impedance measurement reflects minute volume to a much greater extent than stroke volume or motion artifacts. In addition, the impedance measurement reflects minute volume more than signals originating from other physiological and non-physiological sources because of the characteristics of a filter 23 (FIG. 3) which is part of the impedance measurement circuit (see, also, FIG. 1 of the '253 patent). In the preferred embodiment of the invention, the impedance signal is filtered by a two-pole filter with a center frequency of 0.2 Hz. The gain is reduced by a factor of two (6 dB) at frequencies of 0.05 Hz and 0.8 Hz.

Figure 3:
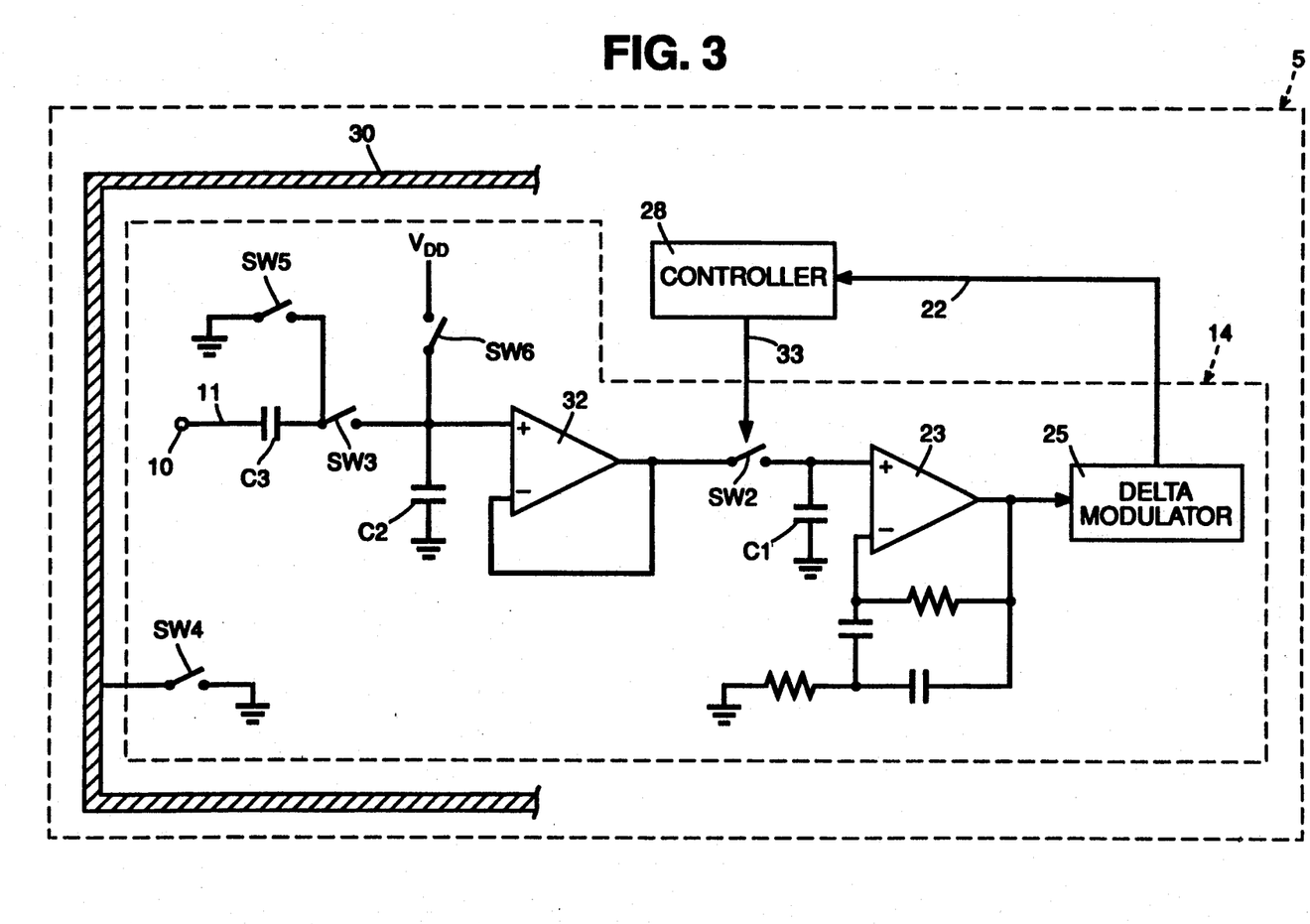
FIG. 3 depicts an embodiment of an impedance measurement circuit, shown in block form in FIG. 1, which operates in a pulsed mode, rather than in a continuous wave mode.

Referring to FIG. 3, an embodiment of the impedance measurement circuit 14 which operates in a pulsed mode is shown. The impedance measurement circuit 14 includes a connection through a switch SW4 with the case 30, and a connection through a switch SW3 with the tip electrode 10 (via the pacing lead 11). The tip electrode 10 is a conventional pacing/sensing electrode. The indifferent electrode is the case 30. The impedance measurement circuit 14 employs the tip electrode 10 and lead 11 both for applying a source measuring current to the patient's body, and for measuring the respiratory impedance between the tip electrode 10, lead 11 and the case 30. A buffer 32 and filter 23 are also employed in circuit 14.

All switches in FIG. 3 are directly or indirectly under the control of controller 28. One output 33 of the controller is shown extending to switch SW2, but it is to be understood that the switches SW3, SW4, SW5 and SW6 are similarly controlled. The controller closes switch SW6 to charge a measuring capacitor C2 to a regulated voltage source $V_{DD}$. Subsequently, the controller opens switch SW6 and closes switches SW3 and SW4 for a predetermined measuring interval $\Delta T$, while switch SW5 is held open, thereby connecting measuring capacitor C2 to lead 11 through a coupling capacitor C3. While the switches SW3 and SW4 are closed, measuring capacitor C2 discharges through capacitor C3 into the lead 11, thereby decreasing the voltage across measuring capacitor C2. The amount by which the voltage across measuring capacitor C2 diminishes depends on the impedance of the lead-tip combination and the impedance of the surrounding tissue. The impedance of the lead-tip combination is known and the impedance of the surrounding tissue is the object of the measurement. Measuring capacitor C2 stores the voltage which buffer 32 later transfers to the measuring circuit. After the predetermined measuring time interval ΔT, the controller 28 opens switches SW3 and SW4, allowing the buffer 32 to access the voltage held on the measuring capacitor C2. This voltage is advanced through the buffer amplifier 32 and switch SW2 (which the controller 28 closes at the time it opens switches SW3 and SW4), and is sampled on capacitor C1 at the input of the filter 23. Then for the next measuring cycle, the controller 28 opens switch SW2 and closes switch SW6 to charge measuring capacitor C2 for the next measurement. In the preferred embodiment of the invention, the controller 28 measures impedance twenty times per second. For each measurement, the controller closes the switches SW3 and SW4 for a pulse duration of 250 ns, during which the voltage across the capacitor C2 is placed on the lead 11. The resistors and capacitors associated with filter 23 pass frequencies between about 0.05 Hz and 0.8 Hz, the standard range for respiratory measurements.

The value of the measuring capacitor C2 is selected to store the range of voltages which result from various body impedances. In one embodiment of the invention, C2 has a capacitance of 4.7 nF.

The coupling capacitor C3 provides for DC isolation for the input to the measuring circuit. In one embodiment of the invention, a coupling capacitor C3 has a value of about 7.5 μF, which effectively eliminates the influence of the DC voltage on measurement results.

The analog signal output of the filter 23 passes to a delta modulator 25 which provides a digital signal output on conductor 22. The digital signal output on conductor 22 is input to the controller 28 for processing, as is hereinafter described in connection with a discussion of FIG. 8. Converting an analog signal to a digital representation by delta modulation is a standard technique. One example of such an operation is illustrated in U.S. Pat. No. 4,692,719 to Robert H. Whigham, entitled "Combined Pacemaker Delta Modulator and Bandpass Filter", which issued on Sep. 8, 1987. The output of the delta modulator 25 is a summation of a series of 0's and 1's which reflect whether the analog signal is decreasing or increasing.

During a measurement interval, controller 28 opens switch SW1b (shown in FIG. 1) to briefly disable pace and sense functions. Although sensing is disabled while the impedance measurement is in operation, the duration of the measurement is on the order of fractions of microseconds, a time so short relative to that of heart signals that disabling sensing during this time is of no importance.

Figure 4:
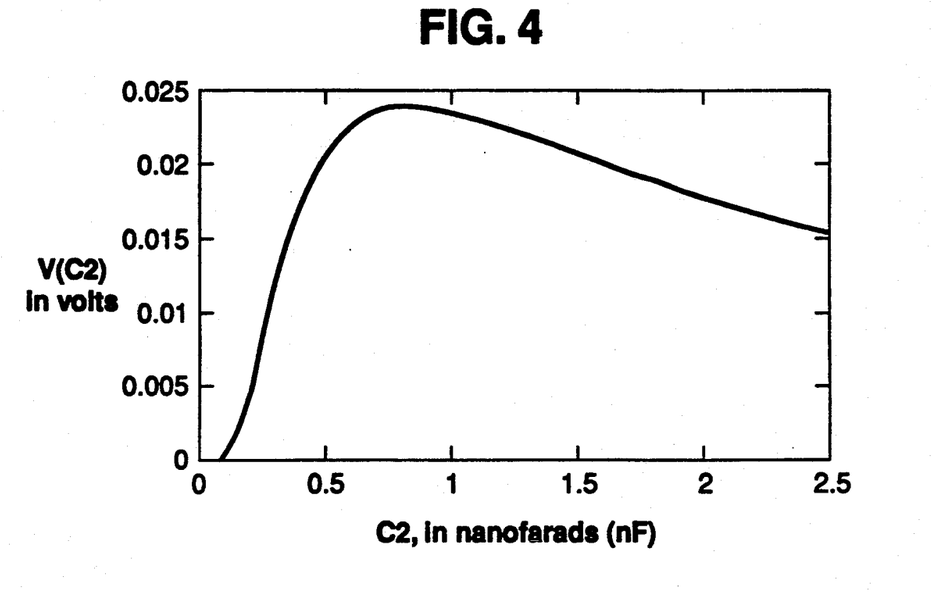
FIG. 4 is a graph which illustrates the amplitude of a desired respiration signal as a function of the source impedance of an impedance measurement circuit similar to the circuit of FIG. 3.

FIG. 4 is a graph which illustrates the voltage amplitude V(C2), in volts, of a respiration signal as a function of the source capacitance (the measuring capacitance C2), in nanofarads, of the impedance measuring circuit of FIG. 3. In particular, FIG. 4 shows, for a given capacitor C2 discharge time (a pulse width of 250 ns), the relationship between the change in voltage on the measuring capacitor C2 with respect to the load impedance and the change in load impedance due to respiration. The purpose of FIG. 4 is to show the importance of matching components of the source impedance of an impedance measuring circuit to the load impedance of the body. FIG. 3 depicts a capacitive discharge circuit which operates best with no impedance between the measuring capacitor C2 and the lead 11. Unfortunately, in an implantable pacemaker, a coupling capacitor C3 is generally perceived to be a requirement to assure safety of the patient. Therefore, the value of the measuring capacitor C2 is selected to best match the source impedance, which includes the measuring capacitor C2, with the load impedance, which includes the impedance of the coupling capacitor C3 and the impedance of the lead 11, in combination with the impedance of the body. The impedance measurement from the FIG. 3 capacitive discharge circuit is derived from a direct measurement of voltage across measuring capacitor C2 as a function of load resistance, the measuring capacitance and the initial voltage across the capacitor. For this capacitive discharge circuit, there exists a preferred measuring capacitance C2 for a given measuring pulse width (for example, 250 ns) and load impedance which will produce a maximum signal voltage V(C2). If the capacitance of the measuring capacitor C2 is very small in comparison to the load impedance of the body, the amplitude of the respiration signal is very small, leading to a modest signal to noise ratio and difficulty in appropriately controlling pacing rate. In contrast, FIG. 4 shows that values of capacitance of the measuring capacitor C2 which are large with respect to load impedance do not greatly diminish the respiratory impedance signal. Therefore, the capacitance of measuring capacitor C2 of an impedance measuring circuit should be equal to or larger than the capacitance which produces a maximum expected respiration signal.

Figure 5:
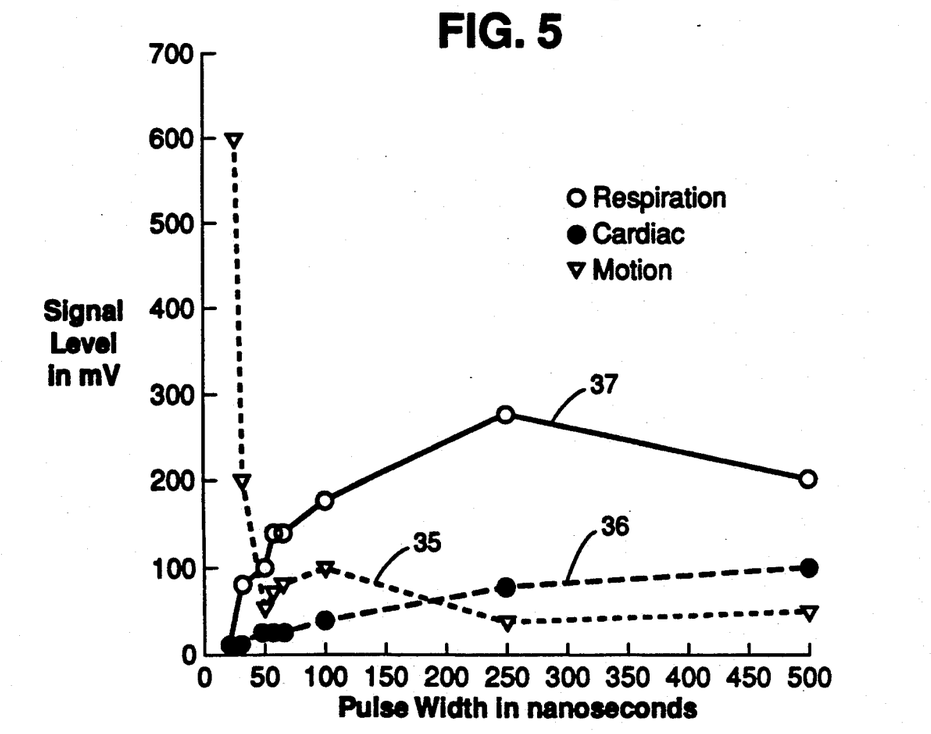
FIG. 5 is a graph which characterizes the relative levels of different physiological and nonphysiological signals which are detected by the circuit of FIG. 3 when it interrogates a patient's body with current pulses of various pulse widths.

The graph of FIG. 5 characterizes the relative levels of different physiological and non-physiological signals which are detected by the circuit of FIG. 3 when it interrogates a patient's body with current pulses of different widths. It illustrates an important advantage of the pacemaker 5 of the present invention. The pacemaker can "tune" the impedance sensor to measure a particular type of signal and reject unwanted signals and other noise by selecting a particular measuring current pulse width. At very short pulse widths (e.g., 60 to 200 nanoseconds) motion artifact signals have the largest amplitude, as shown by "motion" curve 35. The amplitude of physiological signals arising from the heart steadily rises with increasing pulse width duration, as shown by "cardiac" curve 36. The amplitude of respiratory signals abruptly rises with increasing pulse duration to pulse widths of about 250 ns, then decreases for larger pulse width durations, as shown by "respiratory" curve 37. The minute ventilation-controlled metabolic demand pacemaker of the present invention seeks a preferred pulse width of about 250 ns, which provides the best respiratory signal to noise ratio, as is illustrated at 38 in FIG. 6, which figure comprises a graph that illustrates the level of a desired respiratory signal of FIG. 5 relative to a combination of non-respiration "noise" signals of that figure. A pulse width of this duration (250 ns) lessens the influence of cardiac signal "noise", avoids interface electrolytic phenomenon, but still reduces the influence of motion artifacts.

Figure 6:
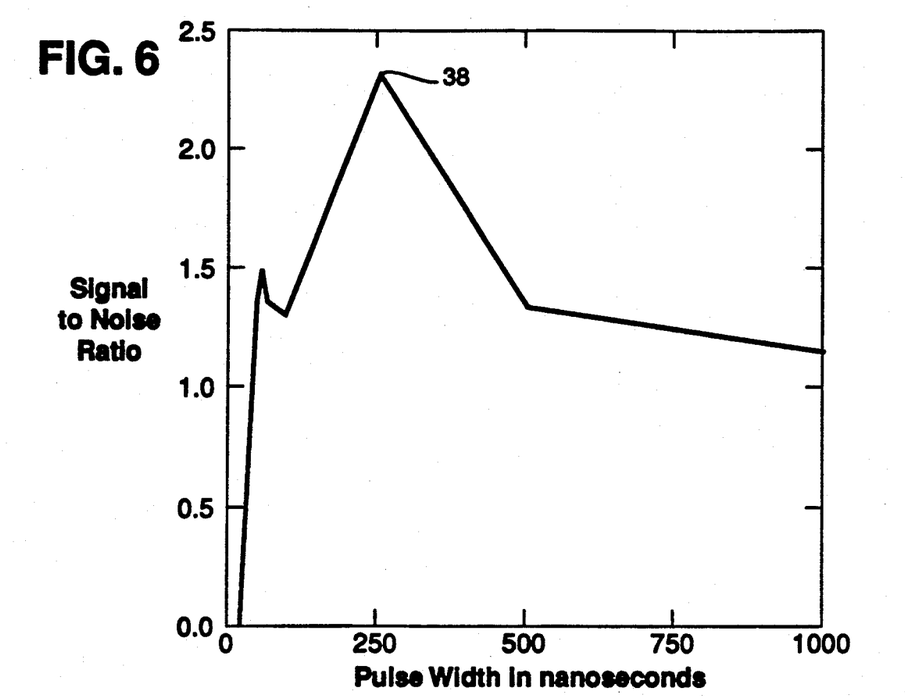
FIG. 6 is a graph which illustrates the level of a desired respiration signal shown in FIG. 5 relative to a combination of non-respiration "noise" signals shown in FIG. 5, as such signals are detected by the circuit of FIG. 3 when it interrogates a patient's body with current pulses of various pulse widths.
Figure 7:
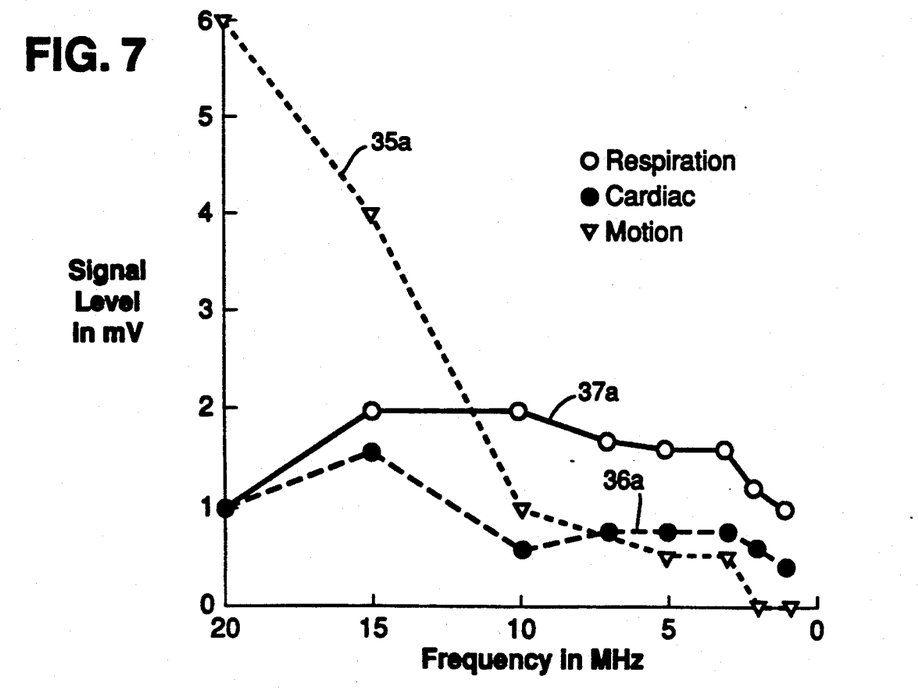
FIG. 7 is a graph which characterizes the relative levels of different physiological and nonphysiological signals as detected by an impedance measurement circuit which interrogates a patient's body with various frequencies of continuous wave current or timed pulses of continuous wave current; and, FIG. 8 depicts circuit blocks contained in a controller, shown in block form in FIG. 1, which operate on digital samples of the impedance measurement to derive pace commands that are sent to a pulse generator, also shown in block form in FIG. 1.

FIGS. 5 and 6 exemplify how different pulse widths provide for differentiation of signals arising from various physiological and non-physiological origins. Similarly, FIG. 7 illustrates this phenomenon in a sensing system which employs continuous wave current modulation rather than current pulses. Shorter pulse widths in a pulsed system have a similar effect upon signal sensing as higher frequencies in a continuous wave system. In general, the pacemaker 5 provides the best respiration signal sensing, in comparison with cardiac and motion noise, when the measuring current frequency is about 2 MHz. At higher frequencies, motion artifacts are large and at lower frequencies, cardiac signals obscure the respiration signal.

The graph of FIG. 7 illustrates the signal amplitude arising from various physiological and non-physiological sources as a function of measuring current continuous wave frequency. "Motion" curve 35a represents the amplitude of motion artifact signals; "cardiac" curve 36a represents the amplitude of physiological signals arising from the heart; and, "respiration" curve 37a represents the amplitude of respiratory signals. The pacemaker may deliver these continuous wave measuring currents in the form of continuous waves or in the form of timed pulses of continuous waves. The measurements resulting from both methods are practically the same. To provide timed pulses of continuous wave measuring current, the pacemaker deactivates the continuous wave current to conserve energy, allow sensing of intracardiac electrograms or provide for generation of pacing pulses. The duration of timed pulses of continuous wave current may range from one cycle of the continuous wave frequency to essentially an infinite duration.

The impedance measurement block 14 of FIG. 1 derives digital spatial impedance samples, in the form of 8-bit data bytes having values ranging from −128 to +127, at a rate of 20 per second and communicates these samples to the controller 28 by means of conductor 22. Negative digital signals carried by the conductor 22 indicate that the analog respiration signal is decreasing, while positive digital signals signify an increasing signal. Referring now to FIG. 8, wherein the circuit blocks of controller 28 are shown in greater detail, the manner in which minute volume is derived from the digital samples provided by impedance block 14 will now be considered. An absolute magnitude extractor 40 derives the absolute magnitude of each digital sample (i.e., negatively signed samples are changed to positive samples of the same amplitude). The average value of the digital samples is zero because the filter 23 (FIG. 3) in the impedance measurement block 14 has a gain of zero for a DC input. By eliminating the sign from all samples, an averager 42 derives a running average of the absolute magnitudes of the samples. The time constant of the averager is short (e.g., about 25 seconds) so that the digital value at its output represents the average respiratory tidal volume over a few breaths. The absolute magnitude value of each sample represents the respiratory impedance signal. Therefore, the controller 28 adds and averages a sequence of these absolute magnitude sample values to provide a measure of the respiratory tidal volume.

A sign extractor 44 monitors only the signs, and not the magnitudes, of the digital samples on conductor 22 to provide for zero crossing detection. The sign extractor 44 delivers successive bits, each of which represents the sign of a digital sample, to a zero crossing detector 46. The zero crossing detector 46 monitors respiration rate by ascertaining the timing of changes in the polarity of the impedance measurement signal. Generally, a zero crossing occurs whenever the sign of a digital sample differs from the sign of the immediately preceding digital sample. However, there are physiological limits to respiration rate and, therefore, to the frequency of zero crossings. Zero crossings occurring at a rate higher than a predetermined physiological limit must indicate the presence of a noisy respiration signal. Thus, the zero crossing detector analyzes the signs of a number (for example 10) of the most recently acquired samples and determines whether a defined preponderance of samples (for example 7 of 10) have a particular sign. If so, and if the last zero crossing operation which found a preponderance of a particular sign determined that the majority had an opposite sign, the zero crossing detector 46 presumes the occurrence of a zero corssing. When the sign changes, the zero crossing detector 46 triggers a sampler 48 to read the average value represented by the current value presented by the averager 42. The sampler 42 delivers this average value to both a short-term averager 50 and a long-term averager 52. In the preferred embodiment of the invention, the short-term averager 50 has a time constant of slightly less than a minute and the long-term averager 52 has a time constant of about one hour.

The zero crossing detector 46 pulses its output twice, and the sampler 48 samples twice, during each breath, when the impedance signal crosses zero during exhalation and during inhalation. The zero crossing detector 46 employs the previously described "majority vote" technique to sense a zero crossing, in which the detector assumes an occurrence of a zero crossing when a predetermined proportion of the most recent samples have a sign opposite to that of the sign determined after the last zero crossing. In the preferred embodiment of the invention, at least 70% of the most recent samples in the last 0.5 second must have a sign opposite to that of the sign determined after the last zero crossing.

Each average value sample at the output of averager 42 represents the tidal volume, the average of the last few integrals of the respiratory impedance signal. The short-term averager 50 and the long-term averager 52 derive values which are dependent not only on the magnitudes of the samples, but also upon the rate of the oscillating respiratory signal, as determined by the zero crossing detector 46. Because the long-term and short-term averagers update and accumulate samples at each zero crossing event, the long-term and short-term minute volume values reflect the rate of breathing as well as the depth of breathing.

As shown in FIG. 8, a summer 54 derives ΔMV, the difference between the short-term averaged and long-term averaged minute volume signals. ΔMV is the control signal which drives the pacing rate. As the short-term average increases relative to the long-term average, representing an increasing metabolic demand, the pacing rate increases. Conversely, when ΔMV decreases, the pacing rate decreases.

The ΔMV value at any instant is the input to a limiter 56, which compares ΔMV to ΔMVMAX, a predetermined value which serves as the maximum ΔMV value allowed to control the pacing rate. The limiter 56 applies the current value of ΔMV, or ΔMVMAX if it is smaller than ΔMV, to the minus input of a summer 58. The summer 58 compares the output of limiter 56 to maximum interval, a quantity applied at the plus input of summer 58 which represents an offset corresponding to a physician-determined minimum pacing rate. Summer 58 continuously presents its output, a difference value, to the input of timer 62, which loads the difference value upon the occurrence of either of two events, a load signal upon conductor 24 or the countdown to zero of timer 62. The sense amplifier 16 of FIG. 1 controls the conductor 24 load signal.

A clock 64 applies pulses to a divider 66, which divides the clock pulses by a quantity referred to as a prescaler. In this manner the pulses, which act upon the decrement input of timer 62, occur at a rate slower than the clock rate. The count in timer 62 decrements whenever a pulse appears at the output of divider 66. When the timer 62 decrements to zero, it produces a pulse upon PACE conductor 26 to trigger activity of the pulse generator 18 in FIG. 1. If the sense amplifier 16 of FIG. 1 senses a natural heartbeat before the timer 62 decrements to zero, the timer will not produce a pulse on PACE conductor 26. In either case, the timer 62 loads the difference value from summer 58 to initialize the escape interval of the pacemaker. The escape interval is the time between a paced or sensed cardiac event and the subsequent pacing stimulus.

In this manner, the pacemaker operates in a standard VVI mode except that the minute volume measurement determines the pacing rate. As the quantity ΔMV increases, the summer 58 derives a smaller difference value ("maximum interval" minus ΔMV) that it presents to timer 62. This, in turn, means that the pacing rate increases, as is required for a larger ΔMV. When ΔMV is zero, the summer 58 presents the maximum interval value to the timer 62, which results in the minimum pacing rate, precisely what is required when there is no metabolic demand beyond that provided by the minimum pacing rate. The quantity "maximum interval" is simply the interval which corresponds to the minimum rate.

Conventional pacemakers include telemetry systems, as represented by block 68 of FIG. 8, which allow a physician to program parameters such as minimum rate, as well as the prescaler value, ΔMVMAX and the reference threshold which is applied to comparator 60 and will be described below. The method of derivation of these programmable parameters is disclosed in the description of the '725 pacemaker.

Again referring to FIG. 8, the output of summer 54 is input, not only to the limiter 56, but also to the plus input of a comparator 60. The telemetrically-programmed reference threshold feeds the minus input of the comparator. Whenever ΔMV exceeds the reference threshold, the output of the comparator goes high and inhibits the long-term averager 52. In effect, a large value of ΔMV represents a metabolic demand which is associated with an exercising patient. Until the patient stops exercising, the long-term average does not increase. If it were allowed to increase, after an hour or more the long-term average would approach the value of the short-term average, ΔMV would diminish and the pacing rate would drop from its original high value. Once the patient begins exercising and the pacing rate increases, it is not desirable that the rate decrease simply due to the elapse of time. For this reason, the pacemaker fixes the long-term average. When the patient stops exercising and the short-term average decreases, ΔMV will fall below the reference threshold and the long-term average will again track the short-term average in the usual manner. In the illustrative embodiment of the invention, the reference threshold is equal to one-half of the ΔMVMAX, unless the physician programs the value differently. This technique allows long-term adaptation to a basal minute volume measurement level while still allowing extended periods of exercise.

From the foregoing discussion, it is apparent that the present invention provides rate-responsive pacing based on measurements of respiratory minute volume which are sensed from a standard unipolar pacing lead. The invention accomplishes substantial improvements in respiration signal fidelity by reducing signals arising from electrical activity of the heart, motion artifacts and noise arising from the electrode-electrolyte interface.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:
1. A rate-responsive pacemaker comprising:
   pulsing means for providing pacing current pulses at a controlled rate;
   a unipolar lead coupled to said pulsing means and having an electrode adapted to couple said pulsing means to a patient's heart for delivering said pacing current pulses to said heart;
   means for periodically applying a measuring current between said lead and a reference point in said pacemaker, said measuring current having frequency components in a range extending from approximately 10 kilohertz to approximately 1000 megahertz;
   means operative during the application of said measuring current between said lead and said reference point for measuring the spatial impedance between said lead and said reference point as a function of the patient's pleural pressure;
   means responsive to said measuring means for determining the patient's minute volume; and
   means coupled to said pulsing means for changing said controlled rate in accordance with the patient's minute volume.

2. A rate-responsive pacemaker according to claim 1, wherein said means for applying a measuring current includes circuitry for generating a constant measuring current.

3. A rate-responsive pacemaker according to claim 1, wherein said means for applying a measuring current includes circuitry for generating a measuring current at a constant voltage.

4. A rate-responsive pacemaker according to claim 1, wherein said measuring current is in the form of short-duration current pulses.

5. A rate-responsive pacemaker according to claim 4, wherein said current pulses have pulse durations ranging from about 5 nanoseconds to about 5 microseconds.

6. A rate-responsive pacemaker according to claim 4, wherein said current pulses have pulse durations which are selected to distinguish and enhance signals arising from at least one particular origin.

7. A rate-responsive pacemaker according to claim 4, wherein said current pulses have pulse durations which are selected to attenuate signals arising from at least one particular origin.

8. A rate-responsive pacemaker according to claim 7, wherein said current pulses have pulse durations which are longer than 50 nanoseconds to attenuate signals arising from motion, and wherein said current pulses have pulse durations which are shorter than 1000 nanoseconds to attenuate signals arising from cardiac electrical signals.

9. A rate-responsive pacemaker according to claim 1, wherein said measuring current is in the form of continuous waves.

10. A rate-responsive pacemaker according to claim 9, wherein said continuous wave current has frequency components in the range from about 10 kilohertz to about 1000 megahertz.

11. A rate-responsive pacemaker according to claim 9, wherein said continuous wave current has frequency components which are selected to distinguish and enhance signals arising from at least one particular origin.

12. A rate-responsive pacemaker according to claim 9, wherein said continuous wave current has frequency components which are selected to attenuate signals arising from at least one particular origin.

13. A rate-responsive pacemaker according to claim 12, wherein, at first predetermined times, said measuring current applying means generates a continuous wave current having frequency components which are greater than 20 megahertz to attenuate signals other than those arising from motion and wherein, at second predetermined times, said measuring current applying means generates a continuous wave current having frequency components which are less than 2 megahertz to attenuate signals other than those arising from cardiac electrical signals.

14. A rate-responsive pacemaker according to claim 1, wherein said measuring current is in the form of timed pulses of continuous waves.

15. A rate-responsive pacemaker according to claim 14, wherein said timed pulses of continuous wave current have frequency components in the range from about 10 kilohertz to about 1000 megahertz.

16. A rate-responsive pacemaker according to claim 14, wherein said timed pulses of continuous wave current have frequency components which are selected to distinguish and enhance signals arising from at least one particular origin.

17. A rate-responsive pacemaker according to claim 14, wherein said timed pulses of continuous wave current have frequency components which are selected to attenuate signals arising from at least one particular origin.

18. A rate-responsive pacemaker according to claim 17, wherein, at first predetermined times, said measuring current applying means generates timed pulses of continuous wave current having frequency components which are greater than 20 megahertz to attenuate signals other than those arising from motion and wherein, at second predetermined times, said measuring current applying means generates timed pulses of continuous wave current having frequency components which are less than 2 megahertz to attenuate signals other than those arising from cardiac electrical signals.

19. A rate-responsive pacemaker according to claim 1, wherein said means for measuring the spatial impedance has a source impedance which is approximately equal to or greater than the load impedance of the patient's body.

20. A rate-responsive pacemaker according to claim 19, wherein said means for measuring the spatial impedance has a source impedance in the range from about 200 ohms to about 600 ohms.

21. A rate-responsive pacemaker according to claim 1, wherein said means for measuring the spatial impedance is a capacitive discharge circuit, and wherein such circuit includes a capacitance which has been selected to provide a maximum measured voltage for a predetermined pulse width and load impedance.

22. A rate-responsive pacemaker according to claim 1, wherein said electrode is adapted to be positioned on the heart wall.

23. A rate-responsive pacemaker comprising:

pulsing means for providing pacing pulses at a controlled rate;

a unipolar lead coupled to said pulsing means and having an electrode adapted to couple said pulsing means to a patient's heart;

means for periodically introducing a measuring current between said lead and a reference point and measuring the voltage across said lead and said reference point to derive a spatial impedance signal; and means coupled to said pulsing means for adjusting said controlled rate as a function of said spatial impedance signal.

24. A rate-responsive pacemaker according to claim 23, wherein said electrode is adapted to be positioned on the heart wall.

25. A rate-responsive pacemaker according to claim 23, wherein said measuring current is in the form of short-duration current pulses.

26. A rate-responsive pacemaker according to claim 25, wherein said current pulses have pulse durations ranging from about 5 nanoseconds to about 5 microseconds.

27. A rate-responsive pacemaker according to claim 25, wherein said current pulses have pulse durations which are selected to distinguish and enhance signals arising from at least one particular origin.

28. A rate-responsive pacemaker according to claim 25, wherein said current pulses have pulse durations which are selected to attenuate signals arising from at least one particular origin.

29. A rate-responsive pacemaker according to claim 28, wherein, at first predetermined times, said measuring current applying means generates current pulses having pulse durations which are shorter than 50 nanoseconds to attenuate signals other than those arising from motion and wherein, at second predetermined times, said measuring current applying means generates current pulses having pulse durations which are longer than 1000 nanoseconds to attenuate signals other than those arising from cardiac electrical signals.

30. A rate-responsive pacemaker according to claim 23, wherein said measuring current is in the form of continuous waves.

31. A rate-responsive pacemaker according to claim 30, wherein said continuous wave current has frequency components ranging from about 10 kilohertz to about 1000 megahertz.

32. A rate-responsive pacemaker according to claim 31, wherein said continuous wave current has frequency components which are selected to distinguish and enhance signals arising from at least one particular origin.

33. A rate-responsive pacemaker according to claim 31, wherein said continuous wave current has frequency components which are selected to attenuate signals arising from at least one particular origin.

34. A rate-responsive pacemaker according to claim 23, wherein said measuring current is in the form of timed pulses of continuous waves.

35. A rate-responsive pacemaker according to claim 34, wherein said timed pulses of continuous wave current have frequency components ranging from about 10 kilohertz to about 1000 megahertz.

36. A rate-responsive pacemaker according to claim 35, wherein said timed pulses of continuous wave current have frequency components which are selected to distinguish and enhance signals arising from at least one particular origin.

37. A rate-responsive pacemaker according to claim 35, wherein said timed pulses of continuous wave current have frequency components which are selected to attenuate signals arising from at least one particular origin.

38. A method for pacing a patient's heart at a controlled pacing rate in accordance with the patient's repiration minute volume signal, comprising the steps of:

providing an implantable pacemaker and a unipolar lead having an electrode for generating and coupling pacing stimulation pulses to the patient's heart;

periodically applying a measuring current between said lead and a reference point in said pacemaker, said measuring current having frequency components in a range of from approximately 10 kilohertz to approximately 1000 megahertz;

measuring the spatial impedance between said lead and said reference point in response to said application of measuring current between the lead and the reference point while the spatial impedance varies as a function of the patient's pleural pressure;

determining the patient's respiratory minute volume based on said spatial impedance measurement; and changing the controlled pacing rate in accordance with the patient's determined minute volume.

39. A method in accordance with claim 38, wherein said measuring current applying step includes the substep of applying a constant measuring current.

40. A method in accordance with claim 38, wherein said measuring current applying step includes the substep of applying a measuring current at a constant voltage.

41. A method in accordance with claim 38, wherein said measuring current applying step includes the substep of applying the measuring current in the form of short-duration current pulses.

42. A method in accordance with claim 38, wherein said measuring current applying step includes the substep of applying the measuring current in the form of short-duration current pulses having pulse durations in the range of from 5 nanoseconds to 5 microseconds.

43. A method in accordance with claim 38, wherein said measuring current applying step includes the substep of applying the measuring current in the form of continuous waves.

44. A method in accordance with claim 38, wherein said measuring current applying step includes the substep of applying the measuring current in the form of continuous waves having a frequency in the range of from 10 kilohertz to 1000 megahertz.

* * * * *